United States Patent
Jalota et al.

(10) Patent No.: US 11,504,447 B2
(45) Date of Patent: Nov. 22, 2022

(54) METHODS OF PRODUCING AN OSTEOINDUCTIVE CALCIUM PHOSPHATE MATERIAL FOR BONE GRAFTING

(71) Applicant: SECADA MEDICAL LLC, Newport Beach, CA (US)

(72) Inventors: Sahil Jalota, Carlsbad, CA (US); Russell Cook, Newport Beach, CA (US)

(73) Assignee: SECADA MEDICAL LLC, Newport Beach, CA (US)

( * ) Notice: Subject to any disclaimer, the term of this patent is extended or adjusted under 35 U.S.C. 154(b) by 61 days.

(21) Appl. No.: 17/004,775

(22) Filed: Aug. 27, 2020

(65) Prior Publication Data

US 2021/0299323 A1 Sep. 30, 2021

Related U.S. Application Data

(63) Continuation of application No. 16/828,583, filed on Mar. 24, 2020, now Pat. No. 10,786,597.

(51) Int. Cl.
*A61L 27/12* (2006.01)
*A61L 27/54* (2006.01)
*A61L 27/36* (2006.01)

(52) U.S. Cl.
CPC ......... *A61L 27/12* (2013.01); *A61L 27/3608* (2013.01); *A61L 27/3687* (2013.01); *A61L 27/3691* (2013.01); *A61L 27/54* (2013.01); *A61L 2300/102* (2013.01); *A61L 2300/11* (2013.01); *A61L 2430/02* (2013.01)

(58) Field of Classification Search
CPC .. A61L 27/12; A61L 27/3687; A61L 27/3691; A61L 27/3608; A61L 27/54; A61L 2300/102; A61L 2300/11; A61L 2530/02; A61K 31/4439; A61K 9/0051; A61K 9/2031; A61K 9/2072
See application file for complete search history.

(56) References Cited

U.S. PATENT DOCUMENTS

| | | |
|---|---|---|
| 6,949,251 B2 | 9/2005 | Dalal et al. |
| 7,758,882 B2 | 7/2010 | Roeder et al. |
| 7,942,934 B2 | 5/2011 | Yuan et al. |
| 8,460,685 B2 | 6/2013 | Yuan et al. |
| 10,064,892 B2 | 9/2018 | De Groot-Barrere et al. |
| 10,561,683 B2 | 2/2020 | De Groot-Barrere et al. |

(Continued)

FOREIGN PATENT DOCUMENTS

| CN | 109133907 A | 1/2019 |
|---|---|---|
| WO | 2015009154 A1 | 1/2015 |

OTHER PUBLICATIONS

Present Perfect Continuous [online] retrieved on Dec. 21, 2021 from: https://www.englishpage.com/verbpage/presentperfectcontinuous.html, 3 pages (Year: 2021).*

(Continued)

*Primary Examiner* — Ernst V Arnold
(74) *Attorney, Agent, or Firm* — Brown Rudnick LLP (57) ABSTRACT

The present invention relates to methods for producing biphasic calcium phosphate materials using chemical processing methods including exposure to peroxides. The resulting materials exhibit an osteoinductive needle-like surface morphology and are useful as artificial bone grafts.

19 Claims, 5 Drawing Sheets

(56) References Cited

U.S. PATENT DOCUMENTS

| | | |
|---|---|---|
| 10,786,597 B1 * | 9/2020 | Jalota .................. A61L 27/54 |
| 2005/0260115 A1 | 11/2005 | Tas |
| 2009/0110743 A1 | 4/2009 | Dalal et al. |
| 2011/0020419 A1 | 1/2011 | Yuan et al. |
| 2013/0165540 A1 | 6/2013 | Delaney et al. |

OTHER PUBLICATIONS

Biernat et al, Influence of low-temperature reaction time on morphology and phase composition of short calcium phosphate whiskers, Processing and Application of Ceramics, 2019;13(1):57-64.

D'Arros et al, Bioactivity of Biphasic Calcium Phosphate Granules, the Control of a Needle-Like Apatite Layer Formation for Further Medical Device Developments, Frontiers in Bioengineering and Biotechnology, Jan. 2020; 7 (articles 462):1-10.

Elliot, J.C., Structure and Chemistry of the Apatites and other Calcium Orthophosphates, Amsterdam: Elsevier, 1994, entire book.

International Search Report and Written Opinion issued in International Application No. PCT/US2020/024473, dated Jun. 15, 2020, 44 pages.

\* cited by examiner

METHODS OF PRODUCING AN OSTEOINDUCTIVE CALCIUM PHOSPHATE MATERIAL FOR BONE GRAFTING

CROSS-REFERENCE TO RELATED APPLICATIONS

This application claims the benefit of, and priority to, U.S. Non-Provisional application Ser. No. 16/828,583, filed Mar. 24, 2020, the content of which is hereby incorporated by reference herein in its entirety.

FIELD OF THE INVENTION

The present disclosure generally relates to methods of producing a bone grafting product and use of such products.

BACKGROUND

Artificial or synthetic bone can be used to repair damaged areas where natural regeneration may not be feasible or practical. The ability to incorporate new bone growth through osteoconductivity and osteoinductivity are important factors in artificial bone materials. Osteoconductivity is the ability to serve as a scaffold for new bone growth while osteoinductivity refers to the ability of graft material to induce de novo bone growth with biomimetic substances, such as bone morphogenetic proteins.

Recent advances in tissue engineering have produced materials such as calcium phosphates that possess both osteoconductive and osteoinductive properties, thereby, providing a suitable bone grafting material. Calcium phosphates may include hydroxyapatite (HA) or beta-tricalcium phosphate (βTCP) or biphasic calcium phosphate (a combination of HA and βTCP). The osteoinductivity of calcium phosphates is a qualitative feature and depends on various material parameters. A way to improve the osteoinductivity of calcium phosphates is through manipulation of its surface morphology including the cultivation of HA needles or nanorods on the material surface instead of the inherent grain-like morphology of the post-sintering starting material.

Current techniques for inducing HA needles or nanorods and increasing osteoinductivity through surface modifications are limited in that they require hydrothermal treatment at high temperatures and pressures (2-4 bar and above 125° C.) and are only able to produce HA needles on βTCP/HA granules with higher concentrations of βTCP (above 80% βTCP).

SUMMARY

The present invention provides methods for preparing biphasic calcium phosphate materials with an osteoinductivity-boosting needle-like or nanorod-like surface morphology using chemical processes including exposure to peroxides (e.g., hydrogen peroxide). Methods of the invention are able to produce the desired needle-like or nanorod-like surface morphology on biphasic calcium phosphate materials of any ratio including βTCP/HA granules with βTCP content below 80% or even 40%. Furthermore, the inclusion of chemical processing methods of the invention avoids the need for higher heat and pressure hydrothermal treatments while still providing the osteoinductivity-increasing surface characteristics. The post-processing surface morphology of the biphasic material of the invention provides increased osteoinductivity and, therefore, a superior artificial bone material suitable for a variety of orthopedic and maxillofacial treatments.

In certain embodiments, chemical processing methods include exposing biphasic calcium phosphate materials to a peroxide (e.g., hydrogen peroxide) for a period sufficient to generate a needle-like or nanorod-like surface morphology on the material. The peroxide exposure may take place at room temperature or temperatures higher than room temperature in a sealed container. This treatment can be performed either before or after hydrothermal treatment. When applied according to the descriptions herein, peroxide exposure can reduce the required temperature, pressure, and/or time of hydrothermal treatments while delivering a bone graft product with high osteoinductivity. Methods of the invention are able to produce the desired needle-like or nanorod-like surface morphology on biphasic calcium phosphate materials of any ratio including βTCP/HA granules with less than 80% βTCP content.

Methods of the invention are compatible with biphasic calcium phosphate starting granules in a variety of sizes (e.g., 0.1-10 mm). Treatment methods may vary depending on the composition of the starting material. For example, biphasic granules consisting of 20% HA and 80% βTCP (20/80 granules) can be subjected to a chemical treatment that requires soaking in hydrogen peroxide at less than 125° C. to develop the desired needle-like or nanorod-like surface morphology while 60/40 granules may first undergo a hydrothermal treatment at temperatures above 125° C. followed by a chemical treatment such as soaking in a hydrogen peroxide solution at temperatures less than 125° C. to replicate the desired needle-like or nanorod-like surface morphology.

Materials of the invention exhibit improved osteoinductivity compared to pre-treatment granules and may be used to induce the formation of bone tissue in a patient alone or in combination with growth factors, cells, or other components. Biphasic calcium phosphate of the invention can have a particle size ranging from about 0.1 mm to about 10 mm and can be used as a medical implant material or tissue scaffold. Granules of the invention may be used in injections with or without a carrier fluid. Alternatively, the material may be formed into a composite of any size and shape depending on the desired application and can be sized on-site to repair a specific bone defect.

Aspects of the invention include methods for producing a bone grafting product including steps of providing a granule comprising hydroxyapatite (HA) and β-tricalcium phosphate (β-TCP) and conducting a process on the granule to produce one or more HA needle-like or nanorod-like protrusions from the surface of the granule, wherein the process comprises soaking the granule in a solution comprising a peroxide. The process may further include hydrothermally treating the granule prior to soaking. The hydrothermal treatment can include autoclaving the granule at about 140° C. The granule may be autoclaved at about 140° C. for about 8 hours.

Steps of the method may further include drying the granule between autoclaving and the soaking step. Granules may comprise about 60% HA and about 40% β-TCP. In various embodiments, the peroxide may be hydrogen peroxide ($H_2O_2$) and the solution may comprise about 50% $H_2O_2$. The soaking step may be performed in a sealed container for about 6 hours according to certain embodiments.

In various embodiments, the hydrothermal treatment may include autoclaving the granules prior to soaking at a temperature more than 125° C. Granules may comprise about 20% HA and about 80% β-TCP. The solution may comprise about 30% $H_2O_2$. Soaking can occur in a sealed container for about 4 hours.

In certain aspects, methods of the invention may include producing a bone grafting product by providing a granule comprising β-tricalcium phosphate (β-TCP) and at least about 60% by weight hydroxyapatite (HA), performing a hydrothermal treatment on the granule, and soaking the granule in a solution comprising a peroxide to thereby produce one or more HA needle-like protrusions from the granule. The treatment may occur in an open container. In various embodiments, the solution may comprise 50% hydrogen peroxide and the soaking can occur for about 6 hours in a closed container.

Aspects of the invention may include a method for producing a bone grafting product by providing a granule comprising β-tricalcium phosphate (β-TCP) and about 20% by weight hydroxyapatite (HA), and soaking the granule in a solution comprising a peroxide to thereby produce one or more HA needle-like protrusions from the granule. In certain embodiments, the solution can include 30% hydrogen peroxide. Soaking can occur for about 4 hours in a closed container.

Materials of the invention may have a porosity ranging from about 50% to about 60% with about 55%-60% consisting of micropores (less than about 3 μm) and about 30%-about 35% being made up of macropores (greater than about 70 μm). Total pore area of treated biphasic calcium phosphate of the invention may be about 3 to 4 m2/g, or higher. The specific surface area (BET) of the materials of the invention may be more than about 2 to 3 m2/g, or higher and may comprise a needle density of about 1 needle/m2 or more. Needle diameters for treated biphasic materials may range between about 100 and 400 nm with median diameters in a range of about 200 to 250 nm. As discussed in the examples below, osteoinductivity of materials of the invention was found to be increased over that of untreated biphasic materials.

DETAILED DESCRIPTION

Methods of preparing bone grafting materials consisting of biphasic calcium phosphate are disclosed herein using chemical processing to induce an osteoinductive needle-like surface morphology through exposure to peroxides. Specifically, the invention relates to treating biphasic calcium phosphate granules to transform the standard post-sintering grain-like surface morphology into a needle-like surface morphology shown to exhibit superior osteoinductivity. Of particular note, methods of the invention produce the needle-like or nanorod-like surface morphology desired for artificial bone grafts without reliance on the high-temperature and pressure hydrothermal treatments of existing techniques. Furthermore, the chemical processing methods of the invention can generate the desired needle-like or nanorod-like surface morphology on granules of any ratio of calcium phosphate to apatite including β-tricalcium phosphate/hydroxyapatite (βTCP/HA) granules with less than 80% or even 40% βTCP content. Previous treatment methods have been unable to consistently produce such a material.

Methods of the invention use chemical treatments including soaking of biphasic calcium phosphate granules in a peroxide solution to generate the desired needle-like or nanorod-like surface morphology without the need for high-temperature or pressure hydrothermal treatments. Further, such chemical processing methods have proven effective on materials with a lower proportion of calcium phosphate to apatite than is possible with current techniques.

Figure 1:
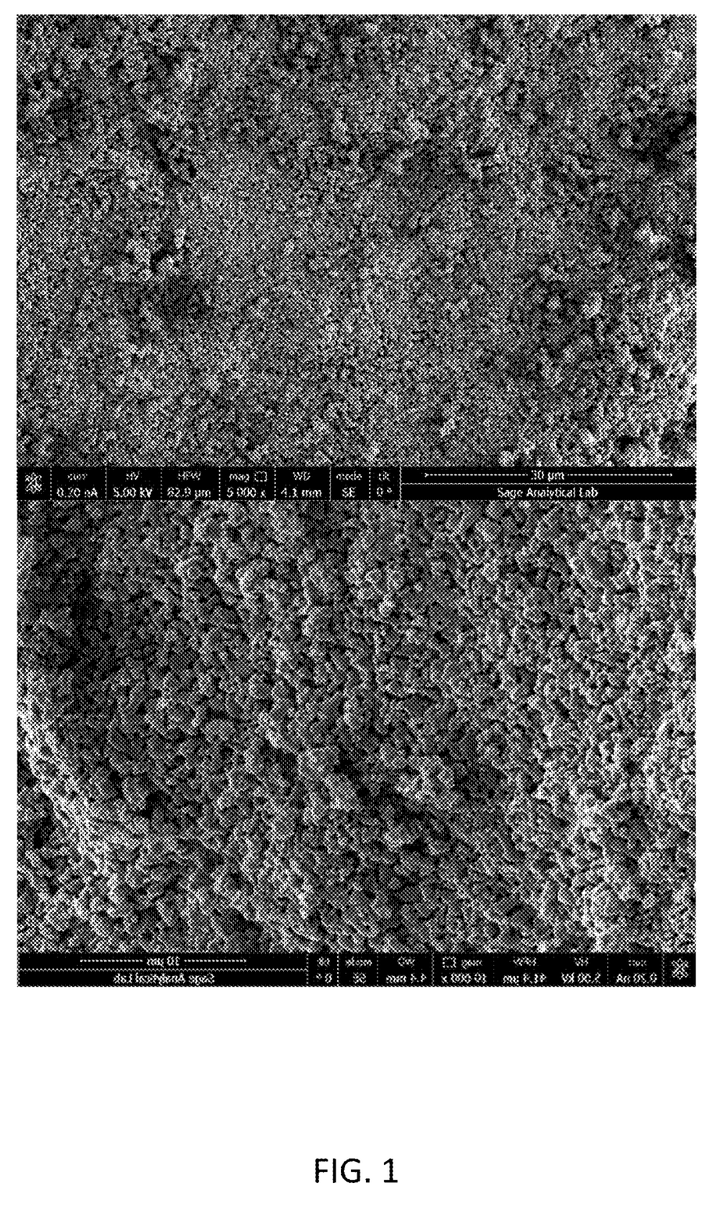
FIG. 1 shows two scanning electron micrograph (SEM) images of post-sintering biphasic granules consisting of 60% HA and 40% βTCP (60/40 granules).
Figure 2:
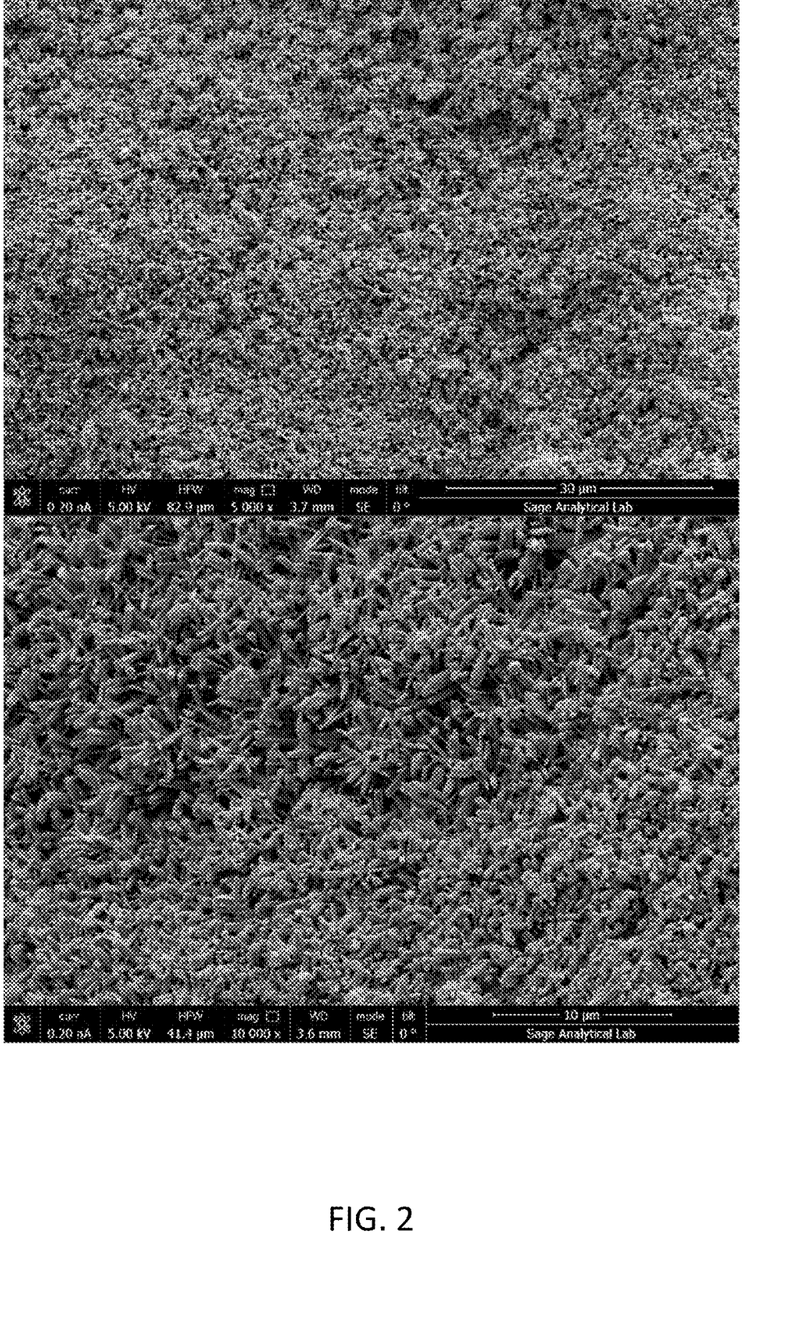
FIG. 2 shows two SEM images of 60/40 granules after processing according to certain methods of the invention.
Figure 3:
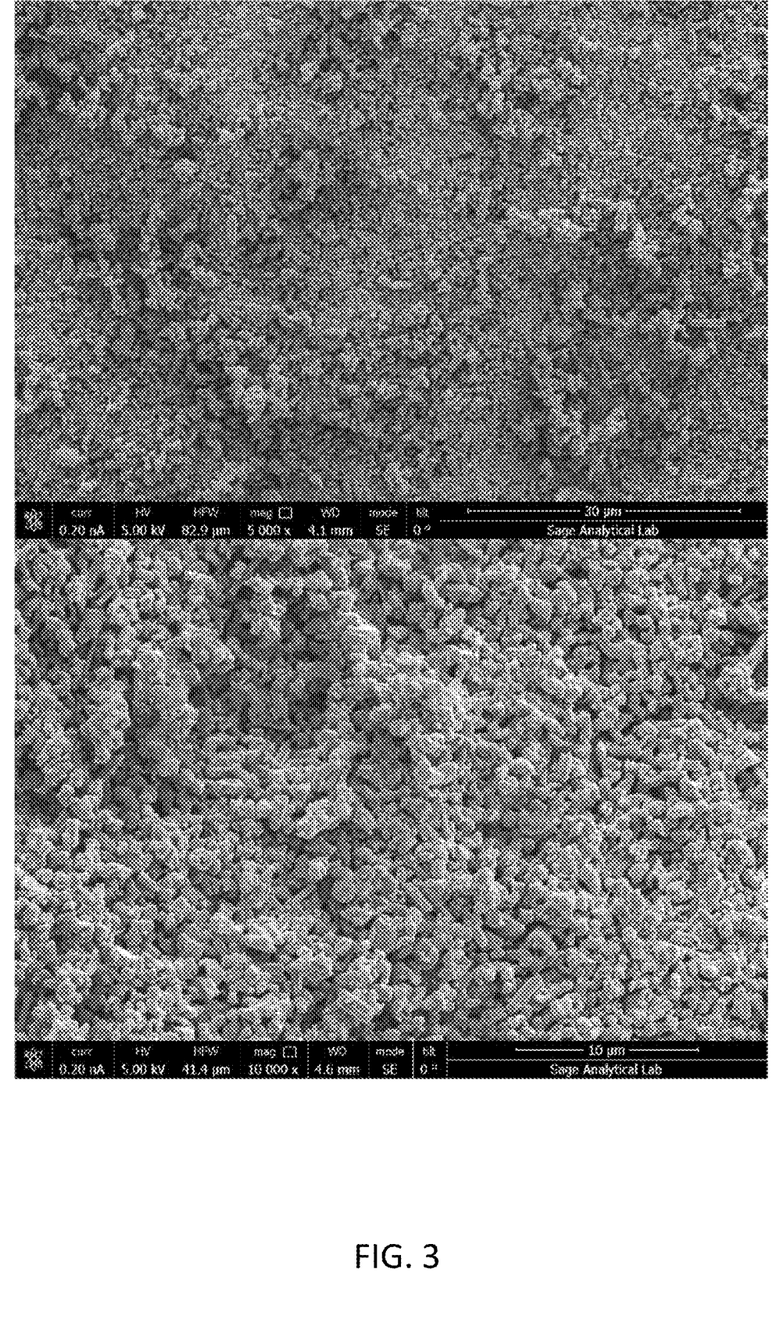
FIG. 3 shows two SEM images of post-sintering biphasic granules consisting of 20% HA and 80% βTCP (20/80 granules).
Figure 4:
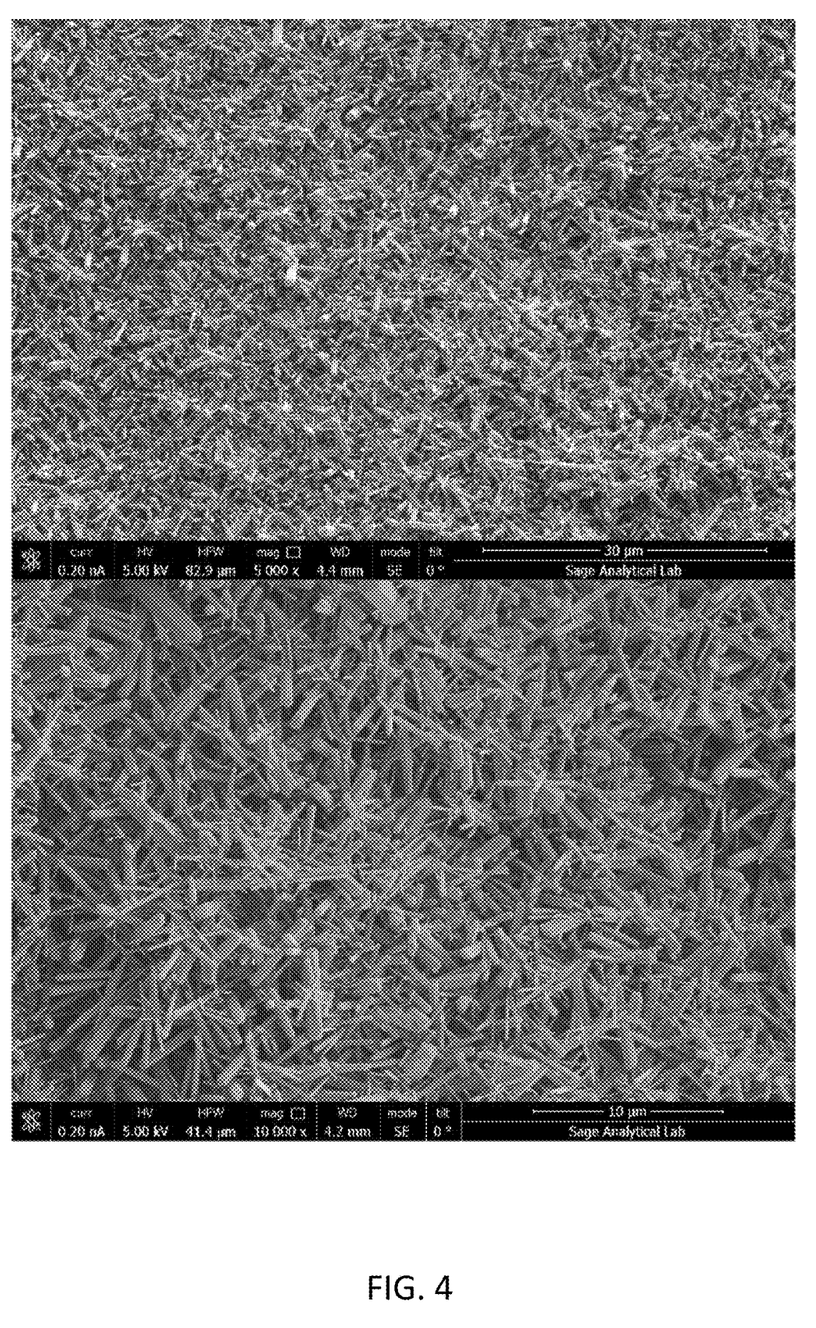
FIG. 4 shows two SEM images of 20/80 granules after processing according to certain methods of the invention.

Needle-like or nanorod-like surface morphology refers to the presence of HA needles or nanorods as shown in FIGS. 2 and 4. Grain-like surface morphology of the post-sintering biphasic calcium phosphate starting granules refers to a relatively smooth surface with a substantial lack of HA needles as shown in FIGS. 1 and 3. Unless otherwise specified, percentages discussed herein with respect to HA and βTCP granule composition refer to percent by weight.

Methods of the invention primarily involve the chemical processing of biphasic calcium phosphate materials using peroxides (along with other optional treatments) to produce a needle-like surface morphology in the material. The soak time and the concentration of peroxide in the solution can vary depending on the type of peroxide used, whether the granules have been hydrothermally treated, and the ratio of HA to βTCP in the granules being processed. For example, in certain embodiments, hydrothermal treated granules having less than 60% βTCP content (e.g., 60/40 granules) may be soaked in a 50% hydrogen peroxide ($H_2O_2$) solution for about 6 hours while granules with higher βTCP content (e.g., 20/80 granules) may be soaked in a 30% $H_2O_2$ solution for about 4 hours to generate the desired needle-like surface morphology. In various embodiments, peroxide treatment may occur in a sealed container.

Peroxides used in processing biphasic calcium phosphate materials are preferably hydrogen peroxide but may be any compound having a peroxide group including peroxy acids, metal peroxides, organic peroxides, and main group peroxides. In certain embodiments, various agents may be substituted for the peroxide in the processing steps described above. Examples include oxidizers, $NaHCO_3$, $Na_2HPO_4$, calcium sulfate, calcite, NaCl, ammonium hydroxide, sodium hydroxide, poly(D,L-lactic-co-glycolic acid), pectin and gelatin, vesicants, cetyltrimethyl ammonium bromide, polytrimethylene carbonate, sucrose, inorganic peroxides, perchloric acid, nitric acid, perborates, periodates, peroxyacids, chlorates, chromate.

In various embodiments peroxide solutions may comprise 3%, 5%, 10%, 20%, 30%, 40%, 50%, 60%, 70%, 80%, 90%, or 100% peroxide and soaking times may be less than about 30 minutes, less than about 60 minutes, less than about 100 minutes, less than about 200 minutes, less than about 300 minutes, less than about 400 minutes, less than about 500 minutes, less than about 600 minutes, less than about 700 minutes, less than about 800 minutes, less than 900 minutes or less than about 1000 minutes.

Biphasic calcium phosphate granules are used as a starting material and can be prepared using known methods.

Such granules are also commercially available in a variety of ratios including the 60/40 and 20/80 HA/βTCP compositions primarily discussed herein.

Methods of the invention contemplate using particles of any size (e.g., 0.1 mm-10 mm) and preferably use sintered biphasic calcium phosphate granules commercially available between 0.5 mm and 2 mm in size. Particles used are preferably sintered biphasic calcium phosphate granules commercially available between 1 mm and 2 mm in size. Methods for preparing biphasic calcium phosphate materials through sintering and the use of foaming and/or porogenic agents (including hydrogen peroxide) are known in the art and described, for example, in U.S. Pat. No. 10,064,892 and U.S. Pat. Pub. No. 20110020419, the contents of each of which are incorporated herein by reference. Additional information on calcium phosphate granules and their use can be found in U.S. Pat. Pub. Nos. 20050260115, 20130165540, and 20090110743 as well as U.S. Pat. Nos. 6,949,251, 8,460,685, and 7,942,934, the contents of each of which are incorporated herein by reference. In various embodiments, starting biphasic calcium phosphate materials may be produced through foaming of an aqueous slurry including a calcium phosphate powder using a foaming agent followed by drying and sintering of the resulting foamed slurry. Particle size of the starting material may be altered by milling of the sintered material to achieve the desired size range.

The ratio of calcium phosphate to hydroxyapatite in the biphasic particles is not a limiting aspect of the invention, and the methods of the invention may be carried out using granules having all different ratios of calcium phosphate to apatite. In certain embodiments, 60/40 HA/βTCP granules may be used as a starting material. After pre-processing according to the invention (or provision of commercially available material), granules have a grain-like morphology with multidirectional interconnected porosity structure, that is about 20-30% microporous (e.g., having a pore size <10 about μm) and 50-55% macroporous. An exemplary scanning electron micrograph (SEM) for such granules is shown in FIG. 1. The grain-like surface morphology along with the microporosity of the material can be seen in the figure. In other embodiments, granules having higher βTCP content (e.g., 20/80 HA/βTCP granules) may be processed using methods of the invention to generate the osteoinductive needle-like or nanorod-like surface morphology. A pre-processing image of exemplary 20/80 granules with mostly grain-like morphologies and some needles is shown in FIG. 3.

While βTCP and HA are discussed herein for purposes of illustrating the methods of the invention, application to other calcium phosphate particles and additional apatite minerals is also contemplated. Other apatite minerals include any calcium phosphate minerals with the repeating stoichiometric chemical formula $Ca_5(PO_4)_3(OH)$ such as hydroxyapatite, fluoro-apatite, chloro-apatite, carbonated apatite or a calcium deficient apatite among others. Elliott, J. C., 1994. Structure and Chemistry of the Apatites and other Calcium Orthophosphates, Amsterdam: Elsevier, incorporated herein by reference.

Processing of bi-phasic calcium phosphate granules may include a hydrothermal treatment the details of which may depend on the ratio of HA to βTCP. Hydrothermal treatment involves exposing the granules to a combination of heat, pressure, and water such as in an autoclave. Hydrothermal treatments may be performed before, after, and/or during chemical processing with peroxide as described above. As noted above, temperature ranges for hydrothermal treatment may depend on the composition of the starting material and can be less than about 125° C. for granules with 60% or more βTCP content and preferably less than about 90° C. Pressure ranges for hydrothermal treatment are preferably between about 2 and 4 bar. For example, in granules having less than 60% βTCP content (e.g., 60/40 granules), hydrothermal treatment may be performed at about 140° C. Treatment may occur, for example, by placing dry granules in an open bottle and then placing in an autoclave. Hydrothermal treatment may be performed at about 140° C. for about 600 minutes in preferred embodiments but longer and shorter treatment times are possible as well and can produce similar results. In various embodiments, temperatures may be less than 125° C., less than 100° C., less than 90° C., less than 75° C., or less than 50° C. Hydrothermal treatment times may be less than about 30 minutes, less than about 60 minutes, less than about 100 minutes, less than about 200 minutes, less than about 300 minutes, less than about 400 minutes, less than about 500 minutes, less than about 600 minutes, less than about 700 minutes, less than about 800 minutes, less than 900 minutes or less than about 1000 minutes. In certain embodiments, a thermal treatment may be used in lieu or in addition to a hydrothermal treatment. For example, dry granules may be treated in an autoclave without any liquid or may simply be heated at atmospheric pressure, in an oven for example.

Hydrothermal treatment can be performed using granules in any liquid. For example, granules may be submerged in an aqueous or non-aqueous solution. Aqueous solutions can include water, hydrogen peroxide, acids, bases, etc. Non-aqueous solutions may include alcohols, etc.

Hydrothermal treatment of bi-phasic calcium with greater βTCP content (e.g., 20/80 granules), can occur at temperatures lower than 140° C., lower than 125° C., and preferably around 90° C. or lower. Such hydrothermal treatments can optionally be performed in an autoclave as described above. Furthermore, hydrothermal treatment may be performed for shorter time periods (e.g., about 4 hours) than for granules with lower βTCP content.

In certain embodiments, hydrothermal treatment is not required and biphasic calcium phosphate granules may begin processing with soaking in a peroxide solution. If a hydrothermal treatment is performed, granules may be recovered and dried before soaking.

After chemical treatment, granules may be rinsed (e.g., with deionized water) and dried before final packaging or use in artificial bone grafts. FIGS. 2 and 4 show SEM images of post-processing 60/40 and 20/80 granules respectively. Notably, granules in both images exhibit a clear development of needle-like or nanorod-like surface morphology subsequent to processing methods of the invention.

While described above primarily with respect to granules, methods of the invention may be applied to surface coatings of biphasic calcium phosphate to similarly generate the desired osteoinductive needle-like or nanorod-like morphology for various implants or other devices. Materials of the invention may have a porosity ranging from about 50% to about 60% with about 55%-60% consisting of micropores (less than about 3 μm) and about 30%-about 35% being made up of macropores (greater than about 70 μm). Total pore area of treated biphasic calcium phosphate of the invention may be about 3 to 4 m2/g, or higher. The specific surface area (BET) of the materials of the invention may be more than about 2 to 3 m2/g, or higher and may comprise a needle density of about 1 needle/m2 or more. Needle diameters for treated biphasic materials may range between about 100 and 400 nm with median diameters in a range of about 200 to 250 nm. Osteoinductivity of materials of the invention is increased over that of untreated biphasic materials.

Materials prepared according to the methods described herein are useful for inducing bone tissue formation in patients including mammals and other organisms. Treated biphasic calcium phosphate can be used as an implant material for medical procedures such as orthopedic surgery and maxillofacial procedures. Bone graft materials of the invention may be used as fillers or scaffolds to facilitate bone formation and promote wound healing and can be used in solid material (block) forms trimmed to fit a certain defect or may be used in a putty or paste (particulated) format. Applications of the materials prepared according to methods of the invention include dental implants (e.g., to restore edentulous area of a missing tooth). In various embodiments, materials of the invention may be used to form large bone sections to restore skeletal integrity to long bones of limbs in which congenital bone defects exist or to replace segments of bone after trauma or malignant tumor invasion. Graft material may also be used to fuse joints to prevent movement, repair broken bones that have bone loss, and repair broken bone that has not yet healed.

EXAMPLES

Example 1: Preparation of Osteoinductive 60/40 HA/βTCP Material with Needle-Like Surface Morphology 60/40 HA/βTCP granules were obtained from Biomatlante. The granules have a grain-like morphology with multidirectional interconnected porosity structure, that is 20-30% microporous (pore size <10 μm) and 50-55% macroporous. The scanning electron micrograph (SEM) for this granule is shown in FIG. 1. Microporosity is clearly visible in the granule along with grain-like surface structure.

The granule was further processed using the following techniques and was subsequently imaged to see the difference in the microstructure:

First, the granules underwent a hydrothermal treatment. The treatment involved placing granules (dry) contained in an open bottle and then placing in an autoclave. The autoclave treatment was performed at 140° C. for 600 minutes. The granules were recovered and dried at 90° C. prior to the next step.

The hydrothermally treated granules were soaked in a 50% hydrogen peroxide ($H_2O_2$) solution in a closed bottle for 6 hours. The granules subsequently washed with deionized water and dried at 90° C. prior to imaging.

The SEM image shown in FIG. 2 demonstrates the change in microstructure from the pristine granules. The image demonstrates needle-like morphology for the treated 60/40 HA/βTCP granules.

Example 2: Preparation of Osteoinductive 20/80 HA/βTCP Material with Needle-Like Surface Morphology The 20/80 HA/βTCP granules are also obtained from Biomatlante. The surface topography of the pristine granules show mostly grains with some needles being present. The SEM image of the pristine granule is shown in FIG. 3.

The granule was further processed using the following technique and was subsequently imaged to see the difference in the microstructure:

First, the granules were soaked in a 30% hydrogen peroxide ($H_2O_2$) solution in a closed bottle for 4 hours. The granules were subsequently washed with deionized water and then dried at 90° C. prior to imaging.

The SEM image shown in FIG. 4 shows the change in microstructure from the pristine granules. The image demonstrates needle-like morphology for the treated 20/80 HA/βTCP granules.

Example 3: Osteoinductive (OI) Potential Testing

Procedure
Experimental Setup

One cc of granules of following groups were implanted in the paraspinal muscles of skeletally mature female sheep:
1. 60/40 HA/βTCP granules 1-2 mm (control)
2. Treated 60/40 HA/βTCP granules 1-2 mm (treatment)
3. Treated 20/80 HA/βTCP granules 1-2 mm (treatment)

The sheep used in the study were greater than 2 years of age and the granules were implanted for a period of 12 weeks in the sheep to evaluate the tissue reaction and osteoinductive property of the treated groups.

Surgical Procedure

Following premedication, an intravenous catheter was placed in a cephalic, jugular, or lateral saphenous vein, and following anesthetic induction, the sheep was endotracheally intubated. IV fluids (Lactated Ringers Solution, or equivalent balanced electrolyte solution at a rate of 2.5-10 mL/kg/hr) were given throughout the procedure. The wool over the back was clipped, and the area was scrubbed with alternating chlorhexidine and isopropyl alcohol for at least three cycles or until the sheep was clean. Once the sheep is positioned prone on the operating table a sterile surgical scrub was performed using chlorhexidine. Prophylactic antibiotics were administered perioperatively. Exposed areas outside of the surgical field were covered as much as possible.

A skin incision, starting at approximately L1 and continuing approximately 10 inches caudally, was made approximately 2 inches off midline on one side of the lumbar spine. The paraspinous muscles was exposed and 6 intramuscular incisions, approximately 1.5 cm in length and 1 inch apart, were made through the fascia and the underlying muscle fibers were separated to create a pocket. One of the 3 graft materials (volume=1.0 ml) were then inserted into the muscle pockets. This procedure was then repeated on the contralateral side of the spine. Once all graft materials were implanted, soft tissues and skin were closed in layers using absorbable suture material.

Following the surgical procedure, anesthesia was terminated and the animal was given appropriate post-operative care prior to transferring to housing pen. The animals will be allowed free movement.

Harvest and Histological Processing

Twelve weeks after implantation, the animals were sacrificed, and the samples were harvested with surrounding tissue. The implant sites were dissected free and removed in tow. The soft tissues were removed, and specimens were placed in 10% neutral buffered formalin (NBF). After adequate fixation time in the 10% NBF, each specimen was decalcified with Cal-Ex, processed in ascending ethanol solutions (70%, 80%, 90%, 95% and 100%×2) and embedded in paraffin for sectioning. Sectioned specimens were stained with H&E and each section was observed under a light microscope (Leitz Photomicroscope with an AO two-headed microscope) to analyze the tissue reaction and bone formation in detail. The sections were graded according to the Edwards scale

TABLE 1

Edwards scale for histological grading

| Grade | Estimated percent of cross-sectional area under review |
|---|---|
| 0 | No evidence of new bone formation |
| 1 | Greater than 0% up to 25% of field shows evidence of new bone formation |
| 2 | 26-50% of field shows evidence of new bone formation |
| 3 | 51-75% of field shows evidence of new bone formation |
| 4 | 76-100% of field shows evidence of new bone formation |

Note:
Final determination of osteoinductive potential as either positive or negative was based solely on the histopathology analysis of the implant sites. This determination included microscopic observations of the criteria listed below (not exhaustive nor exclusive):
Presence of chondroblasts/chondrocytes
Presence of osteoblasts/osteocytes
Presence of cartilage/osteoid
Presence of new bone
Presence of bone marrow Results A total of twelve (12) samples were implanted intramuscularly into the paraspinal muscles of skeletally mature female sheep. There were three groups evaluated in this study with four (4) samples per each group. After 12 weeks, samples were retrieved with their surrounding tissue. No inflammation was seen in any of the explants. Bone formation was observed in varying quantities in all the groups of the study. As per Edwards scale, the osteoinductive potential of the groups were in the following order: Treated 20/80 HA/βTCP>Treated 60/40 HA/βTCP>60/40 HA/βTCP. Average osteoinductivity scores across four implants for each group are shown in Table 2.

TABLE 2

Osteo Inductivity Results

| Group | Osteoinductivity Score |
|---|---|
| 60/40 HA/β-TCP (control) | 1.3 |
| Treated 60/40 HA/β-TCP (Treatment) | 1.7 |
| Treated 20/80 HA/β-TCP (Treatment) | 1.8 |

Figure 5:
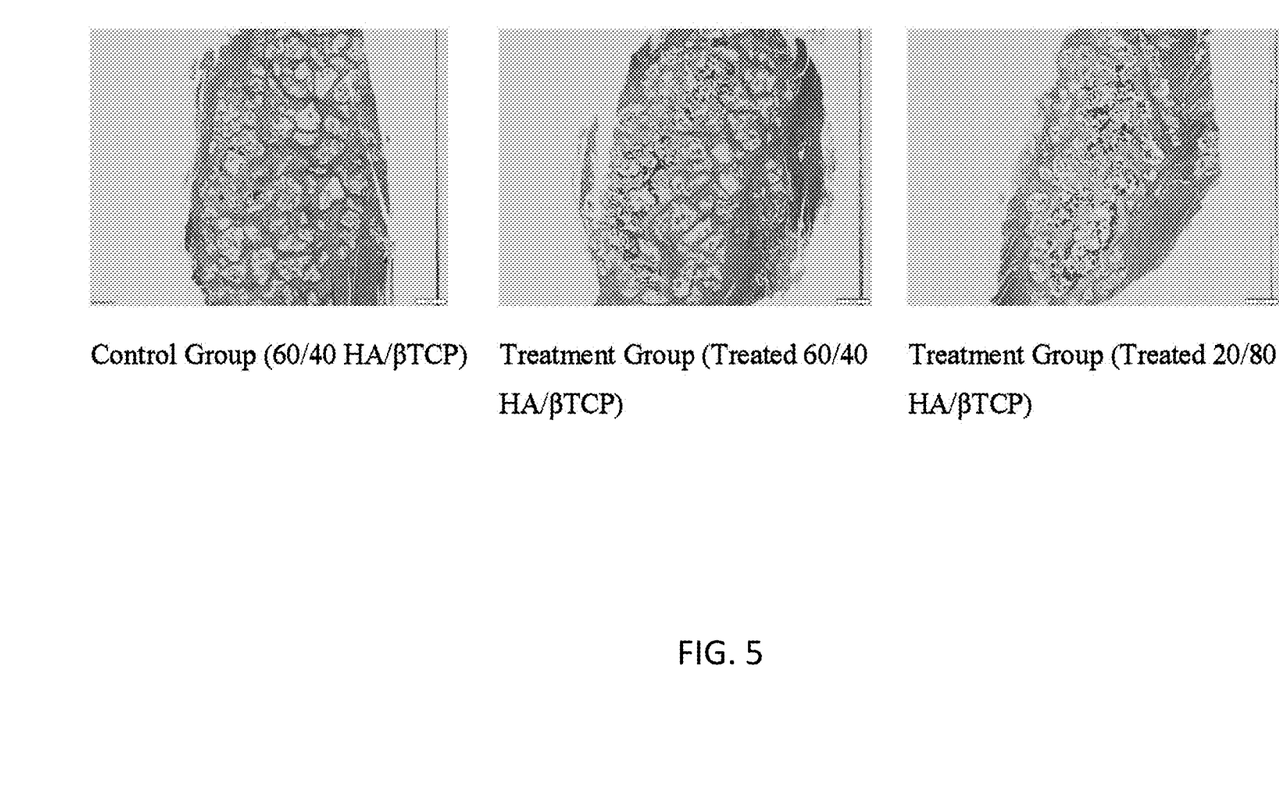
FIG. 5 shows representative histology images for different groups of the study. Treatment groups had more bone formation than the control group.

The representative histological images for the control and two treatment groups are presented in FIG. 5. As shown in Table 2 and FIG. 5, significantly more bone formation was observed in the treatment groups than the control group. The new bone is represented by the darkest staining toward the center of the two treated groups and nearly absent from the control group.

Example 4: Scanning Electron Microscopy

Procedure

Scanning electron microscopy in the secondary electron mode (SEM; JEOL) was used to evaluate the surface topography of the starting granules and the treated granules. After hydrothermal treatment, the diameter of 100 formed needles was measured, and median values were calculated. All measurements were performed with the tool 'length measurement' in ImageJ (v1.43u, NIH, USA) using the SEM scale bar as reference.

Results

The SEM images demonstrated that the grain-like surface as seen on pretreated materials was successfully transformed to needle-like or nanorods-like surface after the peroxide treatment. The diameter data for Treated 60/40 HA/βTCP and Treated 20/80 HA/βTCP is presented in Table 3.

TABLE 3

SEM surface characterization of treated groups

| Sample | Needle Diameter (nm) | Median Diameter (nm) |
|---|---|---|
| Treated 60/40 HA/βTCP | 260 ± 100 | 258 |
| Treated 20/80 HA/βTCP | 235 ± 128 | 196 |

Example 5: BET Surface Area

Procedure

For BET surface area by gas physisorption, the analysis was conducted using the Micromeritics TriStar II instrument. Briefly, a representative aliquot of sample (approximately 2 g) was added to a sample cell with 0.5" neck. To remove moisture from the sample surfaces and pores, the sample was degassed under vacuum at 40° C. for 16 hours prior to analysis. Analysis was conducted at 77.35K using nitrogen gas as the adsorbate. Saturation pressure of nitrogen was measured by the instrument throughout the experiment. Adsorption and desorption process was allowed to equilibrate at each relative pressure (P/P0) for 20 seconds. The surface area was calculated from 5 adsorption points in the P/P0 range of 0.05-0.20 using the BET method.

Results

BET surface area are mentioned in Table 4. The data suggests that the needle-like or nanorod-like formations on the granule surface lead to increase in their specific surface area.

TABLE 4

BET Specific Surface Area measurements before and after treatment for 60/40 HA/βTCP and 20/80 HA/βTCP

| Sample | Treatment | BET Specific Surface Area (m$^2$/g) |
|---|---|---|
| 60/40 HA/βTCP | Pristine | 2.06 |
|  | Treated | 3.18 |
| 20/80 HA/βTCP | Pristine | 2.20 |
|  | Treated | 2.32 |

Example 6: Mercury Intrusion Porosimetry

Procedure

For pore size distribution and porosity by mercury intrusion porosimetry, the analysis was conducted using the Micromeritics AutoPore V instrument. Briefly, a representative aliquot of sample (approximately 0.7 g) was added to a calibrated 5 cc powder penetrometer with a stem volume of 1.131 cc. To remove moisture from the sample surfaces and pores, the sample was evacuated on the instrument at room temperature to a target pressure of 30 μmHg. After further applying vacuum for 5 minutes, the penetrometer bulb was filled with mercury at about 0.5 psia. Pressures of up to around 50,000 psia were applied to force intrusion of mercury into the void space in the sample. Equilibration at each pressure step was monitored by rate of intrusion (0.050 μL/g/sec). Baseline errors are compensated by a blank analysis using the same penetrometer under similar analysis conditions. The pore size distribution results in the range of interest (0.02 to 450 μm) were calculated using the Washburn equation, assuming cylindrical pore structure, 140° for the mercury contact angle, and the appropriate mercury density based on the temperature at the time of analysis.
Results The mercury intrusion porosimetry results are presented in Table 5. The data suggests that there is slight increase in microporosity and the total pore area from the untreated to the treated groups of the same composition.

TABLE 5

BET Specific Surface Area measurements before and after treatment for 60/40 HA/βTCP and 20/80 HA/βTCP

| Sample | Treatment | Macropores >70 μm (%) | Micropores <3 μm (%) | Total Porosity (%) | Total Pore Area (m²/g) |
|---|---|---|---|---|---|
| 60/40 HA/βTCP | Pristine | 41.04 | 52.03 | 55.96 | 2.649 |
|  | Treated | 35.12 | 56.95 | 52.42 | 4.181 |
| 20/80 HA/βTCP | Pristine | 37.51 | 51.05 | 58.15 | 2.81 |
|  | Treated | 33.15 | 54.47 | 58.51 | 2.934 |

Needle Density
Procedure

Needle density on the granule was determined by counting the number of needles visible on a 10000×SEM image (window size 1132.81 um²). The density was calculated per um².
Results The needle density on treated 60/40 HA/βTCP and treated 20/80 HA/βTCP granules were greater than 1 needle/um².

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for inducing bone tissue formation in a patient, the method comprising:
   implanting granules in a patient, the granules comprising more than 20% hydroxyapatite (HA) and less than 80% β-tricalcium phosphate (β-TCP) and comprising one or more HA needle or nanorod protrusions from the granules' surface.

2. The method of claim 1 wherein, the granules have been soaked in a solution comprising an oxidizing agent and, prior to the soaking step, the granules have been hydrothermally treated.

3. The method of claim 2 wherein the hydrothermal treatment comprises autoclaving the granules at about 140° C.

4. The method of claim 3 wherein the granule has been autoclaved at about 140° C. for about 8 hours.

5. The method of claim 4 wherein the granules have been dried between autoclaving and soaking.

6. The method of claim 2 wherein the granules comprise about 60% HA or more and about 40% β-TCP or less.

7. The method of claim 6 wherein the oxidizing agent is hydrogen peroxide ($H_2O_2$).

8. The method of claim 7 wherein the solution comprises about 50% $H_2O_2$.

9. The method of claim 8 wherein the granules have been soaked in a sealed container for about 6 hours.

10. The method of claim 2 wherein the hydrothermal treatment comprises autoclaving the granules at a temperature less than 125° C.

11. The method of claim 10 wherein the oxidizing agent is hydrogen peroxide ($H_2O_2$).

12. The method of claim 11 wherein the solution comprises about 30% $H_2O_2$.

13. The method of claim 12 wherein the granules have been soaked in a sealed container for about 4 hours.

14. The method of claim 1 comprising implanting the granules as a bone graft.

15. The method of claim 1 comprising implanting the granules to promote wound healing.

16. The method of claim 1 comprising implanting the granules in a maxillofacial procedure.

17. The method of claim 1 comprising implanting the granules in a putty or paste format.

18. The method of claim 1 comprising implanting the granules as a solid block of material.

19. The method of claim 18 comprising trimming the solid block of material to fit a bone defect in the patient.

* * * * *